United States Patent [19]
Griffin et al.

[11] Patent Number: 4,568,694
[45] Date of Patent: Feb. 4, 1986

[54] GROWTH-ENHANCING CYSTAMINE DERIVATIVES

[75] Inventors: Richard M. Griffin, Bishops Stortford; Malcolm N. Palfreyman, Upminster, both of England

[73] Assignee: May & Baker Limited, Essex, England

[21] Appl. No.: 504,459

[22] Filed: Jun. 15, 1983

[30] Foreign Application Priority Data

Jun. 16, 1982 [GB] United Kingdom ............... 8217493

[51] Int. Cl.[4] ................ C07C 143/74; C07C 143/78; A61K 31/18
[52] U.S. Cl. ..................................... 514/601; 564/30; 564/34; 564/33; 564/59; 564/94; 564/98; 564/99; 564/104; 564/108; 564/186; 564/500; 260/465 D; 514/588; 514/580; 514/609; 514/610; 514/482; 514/483; 514/526; 514/528; 514/590; 514/616; 514/602; 514/604; 514/605; 560/231
[58] Field of Search ...................... 564/30, 33, 59, 94, 564/98, 99, 104; 424/320, 321, 322; 514/601, 602, 604, 605

[56] References Cited

U.S. PATENT DOCUMENTS 3,428,576 2/1969 Dickinson et al. .............. 564/104 X
4,157,340 6/1979 Crenshaw et al. .................. 564/104
4,314,076 2/1982 Oiry et al. ............................ 564/33

OTHER PUBLICATIONS

Kalopissis et al., CA 71: 101308c, (1969).
Kalopissis et al., CA 76: 103626g, (1972).

*Primary Examiner*—Thomas A. Waltz
*Attorney, Agent, or Firm*—Stevens, Davis, Miller & Mosher

[57] ABSTRACT

Cystamine derivatives of the formula:

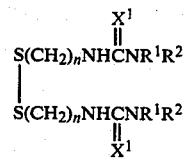

[wherein n represents 2 or 3, $R^1$ and $R^2$ each represents a hydrogen atom, or an alkyl group optionally substituted by a hydroxy, amino, alkylamino or dialkylamino group, or represents a cycloalkyl or aryl group, and $X^1$ represents a group selected from the formulae $=N-CN$, $=N-NO_2$, $=N-COR^3$, $=N-COOR^3$, $=N-NH-CONH_2$, $=N-SO_2R^3$, $=CH-NO_2$, $=CH-SO_2R^3$, $=C(CN)_2$, $=C(CN)COOR^3$ and $=C(CN)CONH_2$ (wherein $R^3$ represents an alkyl or aryl group), or $R^1$ represents a hydrogen atom, $R^2$ represents an alkyl group optionally substituted by a hydroxy, amino, alkylamino or dialkylamino group, or represents a cycloalkyl or aryl group and $X^1$ represents an oxygen or sulphur atom] have been found to be useful in the promotion of the growth of non-human animals including birds.

Prcesses for the preparation of the cystamine derivatives and compositions containing them for administration to non-human animals are described.

18 Claims, No Drawings

GROWTH-ENHANCING CYSTAMINE DERIVATIVES

DESCRIPTION

This invention relates to cystamine derivatives, processes for their preparation, compositions containing them, and their use in the promotion of the growth of non-human animals including birds.

As a result of research and experimentation it has been found that the compounds of the general formula:

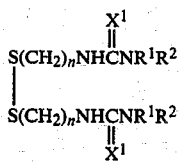

[wherein n represents 2 or 3, $R^1$ and $R^2$ each represents a hydrogen atom, or an alkyl group optionally substituted by a hydroxy, amino, alkylamino or dialkylamino group, or represents a cycloalkyl or aryl group, and $X^1$ represents a group selected from the formulae II to XII:

| | |
|---|---|
| =N—CN | II |
| =N—NO$_2$ | III |
| =N—COR$^3$ | IV |
| =N—COOR$^3$ | V |
| =N—NR—CONH$_2$ | VI |
| =N—SO$_2$R$^3$ | VII |
| =CH—NO$_2$ | VIII |
| =CH—SO$_2$R$^3$ | IX |
| =C(CN)$_2$ | X |
| =C(CN)COOR$^3$ | XI |
| =C(CN)CONH$_2$ | XII |

(wherein $R^3$ represents an alkyl or aryl group), or $R^1$ represents a hydrogen atom and $R^2$ represents an alkyl group optionally substituted by a hydroxy, amino, alkylamino or dialkylamino group, or represents a cycloalkyl or aryl group and $X^1$ represents an oxygen or sulphur atom] and their non-toxic salts possess useful growth promotion activity in respect of non-human animals including birds.

Within the definitions of $R^1$, $R^2$ and $R^3$ in the above formulae, alkyl groups and moieties preferably contain from 1 to 6 carbon atoms, cycloalkyl groups preferably contain from 3 to 8 carbon atoms, and aryl groups are preferably phenyl groups.

Preferred classes of compounds of general formula I comprise those wherein one or more of the following conditions pertain(s):

(i) $X^1$ represents a group of formula II or, more especially, a group of formula VII (wherein $R^3$ is as hereinbefore defined and is preferably a methyl group); and/or (ii) $R^1$ represents a hydrogen atom; and/or (iii) $R^2$ represents a dialkylaminoalkyl, e.g. dimethylaminoethyl, group or, more especially, an alkyl, e.g. methyl, group; and/or (iv) n represents 2; and/or (v) the two halves —S(CH$_2$)$_n$NHC(=X$^1$)NR$^1$R$^2$ of the compound of general formula I are identical.

Compounds of formula I which are particularly important include N,N'-bis(N''-cyano-N'''-dimethylaminoethylamidino)cystamine of the formula:

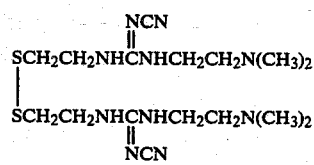

and especially N,N'-bis(N''-methyl-N'''-methylsulphonylamidino)cystamine of the formula:

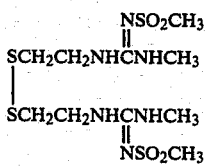

The letters A and B are assigned to the compounds for easy reference later in the specification.

In tests, Compound B showed particularly good performance as a growth promoter in chickens and more especially in pigs.

For example, when administered to cockerels at concentrations of 5, 10, 25 and 50 mg per kg of feed, over 21, 28 or 56 days, Compound B produced significant and consistent improvements in weight gain and in feed/gain ratio (i.e. ratio of weight of food consumed/body weight increase), compared with controls fed on plain feed.

In male and female pigs raised from 20 kg initial weight to at least 64 kg final weight, receiving Compound B at a rate of 25 mg per kg of feed, substantial and significant improvements in average daily weight gain and feed/gain were obtained, compared with controls fed on plain feed, and the time taken to reach a weight of 64 kg was reduced, as shown in the following table:

| | Feed containing Compound B at 25 mg/kg | Plain Feed |
|---|---|---|
| Average daily weight gain (kg body weight) | 0.97 | 0.83 |
| feed/gain ratio | 2.08 | 2.43 |
| Average time to reach 64 kg body weight (days) | 48.2 | 54.5 |

Furthermore, no evidence of any ill effects were found in weaned pigs of either sex which were fed for 28 days on diets containing Compound B at rates up to 250 mg per kg of feed, that is to say enormous doses up to 10 times the usual practical dose level.

Similarly, chicks given Compound B at the enormous oral doses of 2.5 g/kg body weight and observed for 14 days remained normal and no deaths occured.

In rats receiving 14 daily oral doses, Compound B was well tolerated at daily doses of up to 400 mg/kg animal body weight and quite well tolerated at daily doses of 800 or 1600 mg/kg animal body weight.

Compounds of general formula I may be prepared by the application or adaptation of known methods. By the term "known methods", as used in this specification, is meant methods heretofore used or described in the literature.

According to a feature of the present invention, compounds of general formula I, wherein $X^1$ represents a group selected from formulae II to XII and n, $R^1$, $R^2$ and $R^3$ are as hereinbefore defined, are prepared by the reaction between a compound of the general formula:

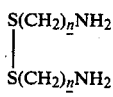

$$\begin{array}{l} S(CH_2)_nNH_2 \\ | \\ S(CH_2)_nNH_2 \end{array} \qquad \text{XIII}$$

(wherein n is as hereinbefore defined) and a compound of the general formula:

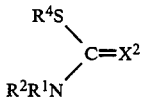

$$\begin{array}{c} R^4S \\ \phantom{R^2R^1N}\diagdown \\ \phantom{R^4S}C=X^2 \\ \phantom{R^2R^1N}\diagup \\ R^2R^1N \end{array} \qquad \text{XIV}$$

wherein $R^1$ and $R^2$ are as hereinbefore defined, $X^2$ represents a group selected from formulae II to XII as hereinbefore defined, and $R^4$ represents an alkyl group containing from 1 to 6 carbon atoms, preferably a methyl group.

Preferably the reaction is carried out in an inert organic solvent, for example an alkanol containing 1 to 4 carbon atoms (e.g. ethanol), acetonitrile, dimethylformamide, dimethylsulphoxide or acetone, at between 0° and 200° C., preferably between 40° and 100° C.

According to a further feature of the present invention, compounds of general formula I, wherein $X^1$ represents an oxygen or sulphur atom and n, $R^1$ and $R^2$ are as hereinbefore defined, are prepared by the reaction of a compound of formula XIII (wherein n is as hereinbefore defined) with a compound of the general formula:

$$R^2NCX^3 \qquad \text{XV}$$

wherein $X^3$ represents an oxygen or sulphur atom and $R^2$ is as hereinbefore defined.

Preferably the reaction is carried out in an inert organic solvent, e.g. acetonitrile, at or near room temperature.

Compounds of general formula XIV may be prepared by the application or adaptation of known methods, for example by the reaction between compounds of the general formulae XVI and XVII:

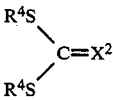

$$\begin{array}{c} R^4S \\ \phantom{R^4S}\diagdown \\ \phantom{R^4S}C=X^2 \\ \phantom{R^4S}\diagup \\ R^4S \end{array} \qquad \text{XVI}$$

$$HNR^1R^2 \qquad \text{XVII}$$

(wherein $R^1$, $R^2$, $R^4$ and $X^2$ are as hereinbefore defined) preferably in an inert organic solvent, e.g. an alkanol containing 1 to 4 carbon atoms, preferably between room temperature and the reflux temperature of the reaction mixture.

As an alternative, when $X^2$ represents a group of formula VIII, the compound of formula XVII is preferably reacted with a sulphoxide of the general formula:

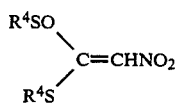

$$\begin{array}{c} R^4SO \\ \phantom{R^4S}\diagdown \\ \phantom{R^4SO}C=CHNO_2 \\ \phantom{R^4S}\diagup \\ R^4S \end{array} \qquad \text{XVIII}$$

wherein $R^4$ is as hereinbefore defined.

Compounds of the formulae XIII, XV, XVI, XVII and XVIII may be prepared by the application or adaptation of known methods.

The non-toxic salts of the cystamine derivatives according to the invention are preferably non-toxic acid addition salts, but other salts of certain compounds of general formula I may also be formed, as will be apparent to those skilled in the art, and the term "salts" in this specification is also meant to embrace chelates of metals.

By the term "non-toxic acid addition salts" as used in this specification is meant acid addition salts the anions of which are relatively innocuous to the animal organism when used in normal doses so that the beneficial veterinary properties of the parent compounds of general formula I are not vitiated by side-effects ascribable to those anions. Similar considerations apply to other non-toxic salts.

As well as being useful in themselves as active compounds, acid addition salts of the compounds of general formula I are useful for the purposes of purification of the parent compounds of formula I, for example by exploitation of the solubility differences between the salts and the parent compounds, by techniques well known to those skilled in the art. The parent compounds of formula I can be regenerated from their acid addition salts by known methods, for example by treatment with an alkali, e.g. aqueous sodium bicarbonate solution or aqueous ammonia solution.

Suitable acid addition salts of the compounds of general formula I for use in growth promotion may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-$\beta$-hydroxynaphthoates, gentisates and di-p-toluoyltartrates.

According to a feature of the present invention, the compounds of general formula I may be converted to their salts by known methods, for example, acid addition salts may be prepared by reaction with the appropriate acid in solution in a suitable solvent, e.g. ethanol, followed if necessary by evaporation of part or all of the solvent, and collection of the solid salt.

It is to be understood that, where in this specification reference is made to the compounds of general formula I, it is intended to refer also, where the context so permits, to salts of the compounds of general formula I.

The following Examples illustrate the preparation of the compounds of general formula I and the Reference Examples illustrate the preparation of intermediates.

EXAMPLE 1

Compound A

A stirred solution of cystamine dihydrochloride (8.9 g) in a mixture of ice and water (30 g) was treated with aqueous sodium hydroxide solution (1N; 80 ml) dropwise during 30 minutes. The resulting mixture was evaporated under vacuum on a water bath at 45° C. and the residue was then subjected to high vacuum for 2 hours. The residue was then treated with isopropanol (60 ml) and the insoluble sodium chloride was filtered off and washed with isopropanol (4×10 ml). The combined filtrate and washings were evaporated. The resulting cystamine residue was dissolved in acetonitrile (30 ml) and treated with a solution of N-cyano-N'-(2-dimethylaminoethyl)-S-methylisothiourea (13.68 g; prepared as described in Reference Example 1) in acetonitrile (50 ml), and the resulting solution was heated at reflux for 24 hours. The solution was evaporated to low volume and the resulting solid was collected and recrystallised from acetonitrile, to give N,N'-bis(N''-cyano-N'''-dimethylaminoethylamidino)cystamine (9.0 g), m.p. 137°–139° C. Elemental analysis: C,44.8; H,7.6;N,32.9;S,15.0%; $C_{16}H_{32}N_{10}S_2$ requires C,44.8;H,7.5;N,32.7;S,14.9%.

EXAMPLE 2

Compound B

Cystamine dihydrochloride (22.5 g) was dissolved in aqueous sodium hydroxide solution (1N; 200 ml) and the solution was evaporated to dryness. The residue was triturated with isopropanol (30 ml), filtered and evaporated to give cystamine in the form of an oil (14.5 g). This oil was dissolved in acetonitrile (300 ml) and treated with N-methyl-N'-methylsulphonyl-S-methylisothiourea (34.3 g; prepared as described in Reference Example 2) and the solution was heated at reflux for 9 hours. After cooling, the solution was evaporated and the residue was crystallised from acetonitrile, to give N,N'-bis(N''-methyl-N'''-methylsulphonylamidino)cystamine (20.8 g), m.p. 141°–143° C. [Elemental analysis: C,28.7; H,6.0;N,20.3;S,30.5%; calculated: C,28.6;H,5.7;N,20.0; S,30.5%].

REFERENCE EXAMPLE 1

A stirred solution of N-cyano-bis(methylthio)methanimine (30 g) in warm ethanol (150 ml) was treated dropwise with 2-dimethylaminoethylamine (24 ml) during 1 hour and stirring was continued for a further period of 3 hours. The resulting white precipitate was recrystallised from ethanol, to give N-cyano-N'-(2-dimethylaminoethyl)-S-methylisothiourea (13.4 g), m.p. 94°–95° C.

REFERENCE EXAMPLE 2

A mixture of N-methylsulphonyl-bis(methylthio)methanimine (188 g) and ethanol (760 ml) was stirred and warmed to 53° C. and the resulting solution was treated dropwise at 45° C. with a solution of methylamine in ethanol (33% w/w; 115 ml) during 2 hours. The solution was then stirred at room temperature for 7 hours and allowed to stand overnight. The solution was concentrated in vacuo to low volume and crystallised from cold ethanol, to give N-methyl-N'-methylsulphonyl-S-methylisothiourea (162 g), m.p. 88°–91° C.

According to another feature of the present invention there is provided a method of improving the growth rate and/or the feed conversion ratio of non-human animals, particularly domestic animals and birds, for example pigs, cattle, e.g. calves, and poultry e.g. chickens and turkeys, by the administration of one or more compounds of general formula I. Such an improvement in the growth rate of the animals means that they attain the desired weight, for example for marketing, in a shorter period of time than is usually necessary or attain a greater weight over the same period of time. It is also found that the administration of one or more compounds of general formula I to the animals improves their feed conversion ratio, that is to say animals receiving one or more compounds of general formula I consume less food to reach a particular weight than similar animals which do not receive a compound of general formula I. When administered to poultry, the compounds of general formula I are also of use in promoting their egg production. The compounds of general formula I will normally be administered in association with a balanced diet.

According to a feature of the present invention, there are provided compositions suitable for administration to non-human animals, including concentrates for addition to their feedstuff or drinking water, comprising at least one compound of general formula I, in association with a physiologically innocuous carrier. By the expression 'physiologically innocuous carrier' as used herein is meant a carrier which is not harmful to the animal. The carrier may be solid or semi-solid or a liquid. Such compositions are conveniently produced by intimately dispersing the active ingredient through the carrier, if necessary, where the carrier is a liquid in which the active substance is but sparingly soluble, e.g. water, using an emulsifying, dispersing, suspending or wetting agent.

Preferred compositions are solids or semi-solids in which the carrier is provided at least in part by a feedstuff, i.e. an organic or mineral substance which is intended to be fed to the animal; that is to say, the active ingredient may be incorporated in a solid or semi-solid feedstuff. Thus, another aspect of the invention is a feedstuff comprising, in an effective amount, at least one compound of general formula I. Incorporation of the active ingredient in the feedstuff may be effected by any conventional method such as stirring, tumbling or grinding. Compositions of varying concentrations can be prepared by altering the ratio of carrier to active ingredient. The active ingredient may also be incorporated in the feedstuff in the form of a powder concentrate containing active ingredient and a solid, physiologically innocuous carrier, e.g. wheat middlings, talc, kaolin or chalk or a diatomaceous earth, such as dieselguhr, or a mixture thereof, and such compositions are also included within the scope of this invention. These compositions may also contain agents to promote adhesion of the active ingredient to the carrier, for example soya oil. To the active ingredient or powders containing it, there may be added before admixture with the feedstuff, one or more physiologically innocuous wetting and/or dispersing agents, for example, the condensation product of β-naphthalenesulphonic acid and formaldehyde, sodium lauryl sulphate or polyoxyethylene (20) sorbitan monooleate. Alternatively, when a wetting, suspending, emulsifying, or dispersing agent is added to the active ingredient or powder, the composition so obtained may be mixed with water to provide stable dispersions suitable for addition to feedstuffs.

Compositions suitable for addition to feedstuffs which comprise the active substance in association with a wetting, suspending, dispersing or emulsifying agent, with or without a physiologically innocuous carrier, are also included within the scope of this invention.

Liquid compositions may be dispersions of the active ingredient in drinking water, and these compositions may be prepared from concentrates which may be added to water or are self-emulsifying with water. Such concentrates comprise the active ingredient in association with a wetting, suspending, dispersing or emulsifying agent, with or without a physiologically innocuous carrier, or in association with a water-soluble physiologically innocuous carrier, and are included within the scope of this invention. Examples of these concentrates are:

(1) mixtures of the active ingredient with a wetting or dispersing agent;
(2) Powders comprising the active ingredient, a physiologically innocuous carrier, and a wetting, suspending or dispersing agent;
(3) Stable dispersions obtained by mixing concentrates of types (1) or (2) with water; and
(4) Mixtures of the active ingredient with a water-soluble physiologically innocuous carrier, e.g. sucrose or glucose.

It is also possible to administer the compounds of the present invention orally in the form of granules, pellets, suspensions, solutions and emulsions comprising the active ingredient in association with suitable physiologically innocuous carriers and adjuvants. Such administration is, however, generally less convenient and therefore such compositions are not preferred.

The compositions of the invention may, if desired, also contain one or more prophylactic or therapeutic agents, for example antibacterials, antibiotics, anthelmintics, anti-fluke drugs and coccidiostats, as well as nutritional additives such as vitamins and mineral salts. Suitable prophylactic and therapeutic agents and nutritional additives are well known in the art and may be selected as desired, provided that they are compatible with the compound or compounds of general formula I and with the other components of the compositions of the invention in which they are to be used.

The compounds of general formula I are administered to the animals at such a rate as may be decided by the farmer, veterinarian, or other person skilled in the art having regard to the species, age, size, sex and condition of the animals, generally at such a rate as to represent between, for example, 5 and 50 mg per kg of feed consumed. As mentioned above, the compounds may be administered via the drinking water or the solid or semi-solid feed.

It will be appreciated that when concentrates in the form of pellets or granules are employed as the means of administration of the active compounds of general formula I the proportion of active compound present in the pellets or granules themselves is considerably higher than the above-mentioned proportions suitable in feedstuffs and that the concentrates can be distributed throughout a feedstuff so as to give, on average over the whole of the feed, an amount of 5 to 50 mg of active compound per kg of feed.

The following Composition Example illustrates compositions according to the present invention.

COMPOSITION EXAMPLE 1

N,N'-Bis(N''-methyl-N'''-methylsulphonylamidino)-cystamine (10.5 g) was added to a mixture of wheat middlings (42 g), soya oil (crude; 2.6 ml) and Embanox 2 (butylated hydroxyanisole; 0.0013 ml) and intimately mixed, then diluted with wheat middlings (997 g) to give a premix containing 1% by weight of active compound. The premix was incorporated in a feedstuff to give a final concentration of 0.0005 to 0.005% by weight of active compound.

We claim:

1. Cystamine derivatives of the formula:

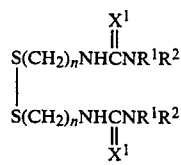

wherein n represents 2 or 3, $R^1$ and $R^2$ each represents a hydrogen atom, or an alkyl group optionally substituted by a hydroxy, amino, alkylamino or dialkylamino group, or represents a cycloalkyl or aryl group, and $X^1$ represents a group $=N-SO_2R^3$, wherein $R^3$ represents an alkyl or aryl group, and their non-toxic salts.

2. Cystamine derivatives according to claim 1 wherein $R^3$ represents methyl.

3. Cystamine derivatives according to claim 1 wherein $R^1$ represents a hydrogen atom.

4. Cystamine derivatives according to claim 1 wherein $R^2$ represents a dialkylaminoalkyl group.

5. Cystamine derivatives according to claim 4 wherein $R^2$ represents a dimethylaminoethyl group.

6. Cystamine derivatives according to claim 1 wherein $R^2$ represents an alkyl group.

7. Cystamine derivatives according to claim 6 wherein $R^2$ represents methyl.

8. Cystamine derivatives according to claim 1 wherein the symbol n in the general formula depicted in claim 1 represents 2.

9. Cystamine derivatives according to claim 1 wherein the two halves $-S(CH_2)_nNHC(=X^1)NR^1R^2$ of the compound of the general formula depicted in claim 1 are identical.

10. Cystamine derivatives according to claim 1 in which alkyl groups or moieties within the definitions of $R^1$, $R^2$ and $R^3$ contain from 1 to 6 carbon atoms, cycloalkyl groups within the definitions of $R^1$ and $R^2$ contain from 3 to 8 carbon atoms, and an aryl group represented by $R^1$, $R^2$ or $R^3$ is phenyl.

11. A cystamine derivative according to claim 1 which is N,N'-bis(N''-methyl-N'''-methylsulphonylamidino)cystamine, and non-toxic salts thereof.

12. A method of improving the growth rate and/or the feed conversion ratio of non-human animals which comprises administering to such an animal at least one cystamine derivative of the general formula specified in claim 1, or a non-toxic salt thereof, in an amount sufficient to improve the growth rate and/or the feed conversion ratio of the animal.

13. A method according to claim 12 wherein the cystamine compound is administered to pigs, cattle or poultry.

14. A method according to claim 13 in which the cystamine compound is administered to calves, chickens or turkeys.

15. Compositions suitable for administration to non-human animals to improve the growth rate and/or the feed conversion ratio, which comprise an effective growth rate and/or feed conversion ratio improving amount of at least one cystamine derivative of the general formula specified in claim 1, or a non-toxic salt thereof, in association with a physiologically innocuous carrier.

16. Compositions suitable for addition to animal feedstuffs, to incorporate therein an effective growth rate and/or feed conversion ratio improving amount of a cystamine derivative of the general formula specified in claim 1, or a non-toxic salt thereof, which compositions comprise a cystamine derivative of the general formula specified in claim 1, or a non-toxic salt thereof, in association with a wetting, suspending, dispersing or emulsifying agent, with or without a physiologically innocuous carrier.

17. Concentrates for addition to drinking water for non-human animals to incorporate therein an effective growth rate and/or feed conversion ratio improving amount of a cystamine derivative of the general formula specified in claim 1, or a non-toxic salt thereof, which compositions comprise a cystamine derivative of the general formula specified in claim 1, or a non-toxic salt thereof, in association with a wetting, suspending, dispersing or emulsifying agent, with or without a physiologically innocuous carrier, or in association with a water-soluble physiologically innocuous carrier.

18. Compositions according to claim 15 which are solid or semi-solid and the carrier is provided at least in part by a feedstuff.

* * * * *